United States Patent [19]

Nakanishi et al.

[11] Patent Number: 4,983,775
[45] Date of Patent: Jan. 8, 1991

[54] NOVEL SUBSTANCES KS-504A, KS-504B, KS-504D AND KS-504E AND PROCESS FOR THEIR PREPARATION

[75] Inventors: Satoshi Nakanishi; Koji Yamada; Katsuhiko Ando, all of Tokyo; Isao Kawamoto, Hiratsuka; Toru Yasuzawa; Hiroshi Sano, both of Tokyo; Noriaki Hirayama, Zama; Hiroshi Kase, Tokyo; Joji Goto, Tokyo; Etsuyo Shimizu, Tokyo, all of Japan

[73] Assignee: Kyowa Hakko Kogyo Co., Ltd., Tokyo, Japan

[21] Appl. No.: 465,893

[22] Filed: Jan. 16, 1990

Related U.S. Application Data

[62] Division of Ser. No. 181,702, Apr. 14, 1988, Pat. No. 4,912,132.

[30] Foreign Application Priority Data

Apr. 15, 1987 [JP] Japan .................................. 62-92815

[51] Int. Cl.$^5$ .............................................. C07C 47/40
[52] U.S. Cl. .................................. 568/446; 568/447; 568/495; 568/838; D 28/1; 514/475
[58] Field of Search ...................... 568/446, 838, 495; D 28/1; 514/475

[56] References Cited

U.S. PATENT DOCUMENTS 3,293,296  12/1966  Paquette ............................. 568/446

OTHER PUBLICATIONS

Nakanshi et al., "Chemical Abstracts", 111:95603w (1989).

Primary Examiner—Werren B. Lone
Attorney, Agent, or Firm—Antonelli, Terry, Stout & Kraus

[57] ABSTRACT

Novel physiologically active substances Ks-504a, KS-504b and KS-504d having a vasodilative activity and a novel physiologically active substance KS-504e having an activity to inhibit histamine secretion are produced by culturing a microorganism of the genus Mollisia.

2 Claims, No Drawings

NOVEL SUBSTANCES KS-504A, KS-504B, KS-504D AND KS-504E AND PROCESS FOR THEIR PREPARATION

This is a divisional of application Ser. No. 181,702, filed Apr. 14, 1988 U.S. Pat. No. 4,912,132.

BACKGROUND OF THE INVENTION

The present invention relates to novel physiologically active substances which are produced by a microorganism belonging to the genus Mollisia, a process for preparing the same and a pharmaceutical composition containing the same.

As the substances having a vasodilative activity which are produced by microorganisms, there are known WS-1228A and WS-1228B which are produced by *Streptomyces aureofaciens* [J. Antibiotics, 35, 151–156 and 157–163 (1982)]; K-259-2 produced by a microorganism belonging to the genus Micromonospora (Japanese Published Unexamined Patent Application No. 63289/86), KS-619-1 produced by a microorganism belonging to the genus Streptomyces (Japanese Published Unexamined Patent Application No. 96987/86), etc. The substances of the present invention having a vasodilative activity are quite different from these substances in structure. Furthermore, no report has been made on substances having a vasodilative activity which are produced by a microorganism belonging to the genus Mollisia.

As the substances having an activity to inhibit histamine secretion which are produced by microorganisms, there are known K-252a [Jpn. J. Pharmacol., 43, 202 (1987)] and KT5556 (Japanese Published Unexamined Patent Application No. 176531/86), which are produced by a microorganism belonging to the genus Nocardiopsis. The substance of the present invention having an activity to inhibit histamine secretion is quite different from these substances in structure. Furthermore, no report has been made on substances having an activity to inhibit histamine secretion which are produced by a microorganism belonging to the genus Mollisia.

Products of a large number of microorganisms isolated from natural habitants have been studied with a view to providing useful novel physiologically active substances which can be used as pharmaceuticals or intermediates therefor. As a result, it has been found that substances having a vasodilative activity and a substance having an activity to inhibit histamine secretion are produced in the culture of a newly isolated microorganism. After isolation and purification of the substances from the culture, their physicochemical properties have been investigated, whereby the substances have been found to be novel physiologically active substances. The substances are hereinafter referred to as KS-504a, KS-504b, KS-504d and KS-504e.

SUMMARY OF THE INVENTION

According to the present invention, novel physiologically active substances KS-504a, KS-504b, KS-504d and KS-504e are produced by culturing a microorganism belonging to the genus Mollisia and being capable of producing the substances in a culture medium until the substances are accumulated in the culture, and recovering the substances therefrom. KS-504a, KS-504b and KS-504d have a vasodilative activity and KS-504e has an activity to inhibit histamine secretion.

DETAILED DESCRIPTION OF THE INVENTION

The present invention provides a novel substance KS-504a represented by the following structural formula (I):

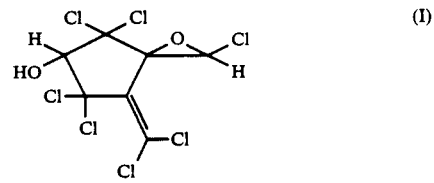

and a novel substance KS-504b represented by the same planar structural formula as the formula (I). The physicochemical properties of KS-504a and KS-504b are as follows.

KS-504a

State: colorless prism-like crystal
Melting point: 102.0°–102.5° C.
Specific rotation: $[\alpha]_D^{24} = -113°$ (C=0.36, methanol)
Molecular formula: $C_7H_3O_2Cl_7$
Solubility:
Soluble: methanol, n-butanol, chloroform, acetone, ethyl acetate, dimethylformamide, dimethylsulfoxide, benzene, acetic acid, hexane
Also soluble in basic substances such as pyridine, monoethanolamine, etc. and alkaline water but readily decomposed.
Insoluble: water, acidic water
Color reaction:
Positive in reaction with iodine and reaction with sulfuric acid; negative in reaction with anisaldehyde, reaction with aniline-phthalic acid, ninhydrin reaction and Reiden-Smith reaction.
Ultraviolet absorption spectrum: $\lambda_{max} = 243$ nm ($\epsilon = 9100$, methanol solution)
Infrared absorption spectrum: (KBr method) 3490, 3100, 2960, 1585, 1400, 1366, 1304, 1288, 1175, 1155, 1135, 1080, 1039, 999, 945, 930, 895, 807, 759, 710, 695, 637, 613, 586 cm$^{-1}$
Elemental analysis: Calculated: C 22.89, H 0.82
Found: C 22.71, H 0.73
NMR spectrum:
$^1$H-NMR: (400 MHz, CDCl$_3$, δ) 6.55 (1H, s), 4.94 (1H, br s), 3.45 (1H, br s)
$^{13}$C-NMR: (25 MHz, CDCl$_3$+CD$_3$OD, δ) 136.9, 130.8, 87.7(2), 85.0, 69.3, 66.7

KS-504b

State: colorless needle crystal
Melting point: 93.0°–93.5° C.
Specific rotation: $[\alpha]_D^{24} = -35°$ (C=0.32, CHCl$_3$)
Molecular formula: $C_7H_3O_2Cl_7$
Solubility:
Soluble: methanol, chloroform, acetone, ethyl acetate, acetonitrile, dimethylsulfoxide
Also soluble in basic substances such as pyridine, monoethanolamine, etc. and alkaline water but readily decomposed.
Insoluble: water, acidic water
Color reaction:
Positive in reaction with iodine and reaction with sulfuric acid; negative in reaction with anisaldehyde, reaction with aniline-phthalic acid, reaction with ferric chloride, ninhydrin reaction and Reiden-Smith reaction.

Ultraviolet absorption spectrum: $\lambda_{max}=241$ nm ($\epsilon=10000$, methanol solution)

Infrared absorption spectrum: ($CHCl_3$) 3550, 3260, 3030, 2960, 2320, 1615, 1605, 1395, 1372, 1287, 1275, 1200, 1178, 1156, 1112, 1080, 994, 955, 938, 900, 830, 815, 715, 662, 630, 610, 498, 455 $cm^{-1}$ NMR spectrum:

$^1$H-NMR: (400 MHz, $CDCl_3$, $\delta$) 5.70 (1H, s), 4.79 (1H, br s), 3.46 (1H, br s)

$^{13}$C-NMR: (100 MHz, $CDCl_3$, $\delta$) 136.1 (s), 127.6 (s), 86.4 (d, J=156 Hz), 86.4 (s), 84.6 (d, J=3.1 Hz) 73.0 (d, J=227 Hz) 70.6 (s)

Mass spectrum:
CI-MS, positive m/z 364(M$^+$)
CI-MS, negative m/z 399(M+Cl)$^-$

KS-504a and KS-504b have the same planar structural formula, and the differences in data of specific rotation and spectra show that the two substances are diastereoisomers. Hereinafter, KS-504a and KS-504b are sometimes generically referred to as KS-504A.

Further, the present invention provides novel substances KS-504d and KS-504e represented by the following structural formulae (II) and (III), respectively:

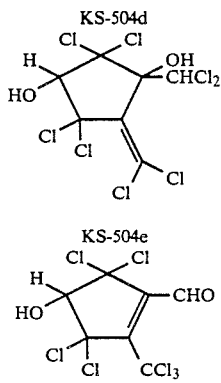

The physicochemical properties of KS-504d and KS-504e are as follows.

State: colorless powder
Melting point: 78.0°-79.0° C.
Specific rotation: $[\alpha]_D^{24}=+4.8°$ (C=0.32, $CHCl_3$)
Molecular formula: $C_7H_4O_2Cl_8$
Solubility:
Soluble: acetone, ethyl acetate, acetonitrile, benzene, methanol, chloroform, hexane, water, acidic water
Also soluble in basic substances such as pyridine, monoethanolamine, etc. and alkaline water but readily decomposed.
Color reaction:
Positive in reaction with iodine and reaction with sulfuric acid; negative in reaction with anisaldehyde, reaction with aniline-phthalic acid, reaction with ferric chloride, ninhydrin reaction and Reiden-Smith reaction.

Ultraviolet absorption spectrum: $\lambda_{max}=237$ nm ($\epsilon=2700$, methanol solution)

Infrared absorption spectrum: ($CHCl_3$) 3540, 3300, 3050, 1592, 1395, 1315, 1278, 1150, 1108, 1060, 960, 927, 888, 815, 682, 648, 605, 530 $cm^{-1}$ NMR-spectrum:

$^1$-NMR: (100 MHz, $CDCl_3$, $\delta$) 6.80 (1H, s), 4.91 (1H, br d, J=12.0 Hz), 3.87 (1H, br s), 3.50 (1H, br d, J=12.0 Hz)

$^{13}$C-NMR: (100 MHz, $CDCl_3$, $\delta$) 137.9 (s), 134.7 (s), 93.2 (s), 86.3 (dd, J=156, 3.1 Hz), 85.5 (d, J=10 Hz), 85.2 (s), 73.1 (d, J=18 Hz)

Mass spectrum:
CI-MS, positive m/z 383 (M-$H_2O$+H)$^+$, 365 (M-HCl+H)$^+$
CI-MS, negative m/z 434 (M-H+Cl)$^-$, 399 (M-H)$^-$ KS504e State: Colorless prism-like crystal
Melting point: 89.0°-89.5° C.
Specific rotation: $[\alpha]_D^{21}=+9.0°$ (C=0.34, $CHCl_3$)
Molecular formula: $C_7H_3O_2Cl_7$
Solubility:
Soluble: methanol, chloroform, acetone, ethyl acetate, acetonitrile, dimethylsulfoxide
Also soluble in basic substances such as pyridine, monoethanolamine, etc. and alkaline water but readily decomposed.
Insoluble: water, acidic water
Color reaction:
Positive in reaction with iodine and reaction with sulfuric acid; negative in reaction with anisaldehyde, reaction with aniline-phthalic acid, reaction with ferric chloride, ninhydrin reaction and Reiden-Smith reaction.

Ultraviolet absorption spectrum: $\lambda_{max}=221$ nm ($\epsilon=5200$, methanol solution)

Infrared absorption spectrum: ($CHCl_3$) 3450, 1748, 1723, 1695, 1620, 1393, 1288, 1260, 1200, 1160, 875, 765, 609 $cm^{-1}$ NMR-spectrum:

$^1$H-NMR: (400 MHz, $CDCl_3$, $\delta$) 10.46 (1H, s), 4.97 (1H, br s), 3.57 (1H, br s)

$^{13}$C-NMR: (100 MHz, $CDCl_3$, $\delta$) 184.3 (d), 148.0 (s), 139.0 (s), 89.0 (d), 88.9 (s), 86.4 (s), 83.9 (s)

Mass spectrum:
CI-MS, positive m/z 365 (M+H)$^+$
CI-MS, negative m/z 399 (M+Cl)$^-$ RF values in thin layer chromatography of KS-504a, KS-504b, KS-504d and KS-504e with various developing solvents are shown in Table 1. Detection was carried out under ultraviolet lamp at 253.7 nm.

TABLE 1

| Plate | Solvent | Rf value | | | |
|---|---|---|---|---|---|
| | | KS-504a | KS-504b | KS-504d | KS-504e |
| Silica gel 60F$_{254}$* | Chloroform | 0.48 | 0.39 | 0.14 | 0.35 |
| Silica gel 60F$_{254}$* | Hexane | 0.00 | 0.00 | 0.00 | 0.00 |
| RP-18 F$_{254}$S** | 90% Methanol | 0.57 | 0.57 | 0.71 | 0.75 |

*Art 5628 manufactured by Merck Inc.
**Art 13724 manufactured by Merck Inc. Development: room temperature, ascending method, 15–40 minutes Development: room temperature, ascending method, 15–40 minutes KS-504A and KS-504d have a vasodilative activity as demonstrated by Experimental Example 1 described hereinbelow and are expected to be utilized as vasodilators.

Further, KS-504e has an activity to inhibit histamine secretion as demonstrated by Experimental Example 2 described hereinbelow and is expected to be utilized as an antiallergic agent and an antiinflammatory agent.

The process for preparing KS-504A, KS-504d and KS-504e is described below.

KS-504A, KS-504d and KS-504e can be produced by culturing a microorganism belonging to the genus Mollisia and capable of producing KS-504A, KS-504d and KS-504e in a medium until the substances are accumulated in the culture, and recovering the substances from the culture.

In the process of the present invention, any microorganism can be used as long as it belongs to the genus Mollisia and is capable of producing at least one member selected from KS-504a, KS-504b, KS-504d and KS-504e. As a specific example, *Mollisia ventosa* KAC-1148 strain (hereafter referred to as KAC-1148) may be mentioned. KAC-1148 was obtained by the present inventors by isolating single ascospores from asci of the apothecia formed on fallen branches collected in Hokkaido. Mycological characteristics of KAC-1148 are as follows.

When the strain is cultured at 20° C. for 4 weeks in malt extract agar medium, a diameter of a colony reaches 3 to 3.5 cm. The colony shows pale brown or pale greyish brown. Hyphae are septate and well branched and extend in and on the medium. Neither teleomorph nor anamorph is observed on the medium.

The strain can grow in a temperature range of 5° to 25° C., and the optimum growth temperature is 15° to 20° C. The pH range in which the strain can grow is 2–11 and the optimum growth pH is 5–7.

The fruit body (apothecium) from which KAC-1148 was isolated is 1 to 2 mm in diameter, and is greyish yellow or cream, with a greyish brown periphery. The margin of the apothecium is composed of textura globulosa and its mycelia show a dark color. The interior of the apothecium is composed of textura intricata. Asci are arranged in an exposed hymenium. There are colorless paraphyses between the asci. The ascus is clavate, 80 to 90 μm in length, with pore blued by iodine, and contains 8 ascospores. Matured ascospores are long ellipsoidal or cylindrical, colorless and smooth, and some of them are slightly curved. The ascospore is fourcelled, 16.5 to 22 μm in length and 2 to 2.5 μm in width.

From the foregoing mycological properties, KAC-1148 was identified to be *Mollisia ventosa*.

The present inventors named this strain *Mollisia ventosa* KAC-1148, which was deposited with the Fermentation Research Institute, Agency of Industrial Science and Technology of Japan under FERM BP-1333 on Apr. 3, 1987.

For the culturing of the microorganism, ordinary culture methods used for the culturing of fungi are generally used. As the medium, any of natural and synthetic media can be used as long as they appropriately contain carbon sources, nitrogen sources, inorganic matters, etc. which the microorganism can assimilate.

As the carbon source, carbohydrates such as glucose, fructose, sucrose, lactose, stabilose, starch, dextrin, mannose, maltose, molasses and an instant mashed potato; organic acids such as citric acid, malic acid, acetic acid and fumaric acid; alcohols such as methanol and ethanol; hydrocarbons such as methane, ethane, propane and n-paraffin; amino acids such as glutamic acid; glycerol, cottonseed oil, etc. can be used.

As the nitrogen source, ammonium salts such as ammonium chloride, ammonium sulfate, ammonium nitrate and ammonium phosphate; amino acids such as aspartic acid, glutamine, cystine and alanine; urea, malt extract, peptone, meat extract, yeast extract, dry yeast, corn steep liquor, soybean powder, cottonseed cake, soybean casein, Casamino acid, pharmamedia, soluble vegetable protein, vegetable or fruit juice, etc. can be used.

As the inorganic matters, potassium dihydrogen phosphate, disodium hydrogen phosphate, magnesium phosphate, magnesium sulfate, ferrous sulfate, manganese sulfate, cobalt sulfate, zinc sulfate, calcium panthothenate, ammonium molybdate, aluminium potassium sulfate, barium carbonate, calcium carbonate, cobalt chloride, magnesium chloride, potassium chloride, sodium chloride, etc. can be used. In particular, compounds containing chloride are essentially required for the production of KS-504A, KS-504d and KS-504e.

In addition, substances capable of promoting the growth of microbial cells or the production of KS-504A, KS-504d and KS-504e such as vitamins may also be added to the medium, if necessary.

When the microorganism to be used requires a specific substance for the growth, it is necessary to add the substance to the medium.

Culturing is carried out at a temperature of 15° to 25° C. at pH around neutrality by shaking culture, aeration-stirring culture, etc. Accumulation of KS-504A, KS-504d and KS-504e reaches the maximum by culturing for 3 to 10 days, and the culturing is completed.

For isolation and purification of the accumulated KS-504A, KS-504d and KS-504e from the culture, conventional methods for the recovery of a physiologically active substance from the culture can be employed.

That is, KS-504A, KS-504d and KS-504e can be isolated by extraction from the cells with solvents such as acetone and methanol; removal of the cells through filtration, centrifugation, etc.; partition with water or organic solvents; and adsorption and desorption treatments of the active substances by column chromatography or thin layer chromatography using adsorptive resins, silica gel, silanized silica gel, alumina, cellulose, diatomaceous earth, magnesium silicate, gel filtering agents, etc.

An example of the process for isolating KS-504a from the culture is given below.

A solvent such as methanol is added to the culture. After the mixture is thoroughly stirred, the cells are separated from the mixture by filtration or centrifugation. The obtained filtrate or supernatant is treated with adsorptive resins, for example, Diaion HP-20 (a product of Mitsubishi Chemical Industries Ltd.), whereby the active substance is adsorbed on the resin. The active substance is eluted with a suitable solvent such as methanol. The eluate is concentrated under reduced pressure to obtain an aqueous solution. A suitable water-immiscible solvent such as ethyl acetate or n-butanol is added to this aqueous solution to extract the active substance. After the extract is concentrated under reduced pressure, silica gel chromatography is repeatedly carried out to give crude KS-504a powder. The crude powder is dissolved in a suitable solvent such as hexane, and the solution is crystallized to give crystals of KS-504a.

During the purification step described above, detection of KS-504a is carried out by thin layer chromatography using a silica gel plate containing a fluorescence agent, followed by ultraviolet irradiation at 254 nm.

KS-504b, KS-504d and KS-504e can be isolated by the method similar to that of isolation of KS-504a.

Further, KS-504e can also be obtained by heating and refluxing KS-504a in the presence of an acid such as hydrochloric acid. As the reaction solvent, anhydrous ethyl acetate, chloroform, dichloromethane, etc. can be used. The reaction is carried out at a temperature from room temperature to 75° C. for several hours to one day. Isolation and purification of the reaction products can be carried out by combinations of extraction, crystallization, chromatography, etc.

KS-504A, and KS-504d have a vasodilative activity and thus are expected to be useful as vasodilators. Further, KS-504e has an activity to inhibit histamine secretion and thus is expected to be useful as an antiallergic agent and an antiinflammatory agent.

Thus, according to a further feature of the present invention, there is provided a pharmaceutical composition comprising, as the active ingredient, an effective amount of at least one member selected from KS-504a, KS-504b and KS-504d or KS-504e and usually at least one pharmaceutically acceptable carrier or excipient.

The pharmaceutical composition may be administered through oral or parenteral route (for example, injection, application, and inhalation). KS-504a, KS-504b, KS-504d and KS-504e can be administered as such, but generally administered in the form of tablets, pills, powder, granules, capsules, suppository, injection, etc. Conventional pharmaceutically acceptable carriers can be used for medical compositions of this invention. They include lactose, dextrose, sucrose, sorbitol, mannitol, glucose, cellulose, cyclodextrin, talc, starch, methylcellulose, gelatin, arabic gum, polyethylene glycol, carboxymethylcellulose, hydroxypropylcellulose, sodium benzoate, sodium hydrogensulfite, aluminium stearate, magnesium stearate, mineral oil, vegetable oil, white vaseline ®, liquid paraffin, etc., and can be appropriately selected in view of the kind of preparations. The present composition can contain 0.01-85 weight percent of KS-504a, KS-504b, KS-504d or KS-504e. The minimal lethal dose of KS-504a in mice is 300 mg/Kg.p.o Certain specific embodiments of the present invention are illustrated by the following examples.

EXAMPLE 1

*Mollisia ventosa* KAC-1148 (FERM BP-1333) was used as the seed strain. The strain was inoculated into 40 ml of a seed medium (pH 6.0) containing 1.0 g/dl glucose, 0.5 g/dl peptone (a product of Kyokuto Pharmaceutical Industry Co., Ltd.), 0.5 g/dl dry yeast Ebios (a product of Asahi Breweries, Ltd.), 0.2 dl/dl V-8 Vegetable Juice (a product of Campbell Co.) and 0.3 g/dl calcium carbonate, and subjected to shaking culture at 25° C. until the strain sufficiently grew. Then, 40 ml of the seed culture was inoculated into 360 ml of the seed medium having the composition described above, followed by shaking culture at 25° C. for 2 days. The thus obtained seed culture (1.8 l was inoculated into 18 l of a production medium described below in a 30 l-jar fermentor.

Production medium: 5.0 g/dl sucrose, 2.0 g/dl soybean powder, 1.0 g/dl corn steep liquor, 8.0 g/dl $MgCl_2 \cdot 6H_2O$ and 0.05 g/dl $Mg_3(PO_4)_2 \cdot 8H_2O$ (pH 6.5)

Culturing was carried out at 25° C. for 7 days with stirring and aeration. After the completion of culturing, an equal volume of methanol was added to the culture, followed by thorough stirring. Then, the cells were removed by filtration with suction and 40 l of the filtrate obtained was passed through a column packed with 500 ml of Diaion HP-20 (a product of Mitsubishi Chemical Industries, Ltd.), whereby KS-504a, KS-504b, KS-504d and KS-504e were adsorbed on the resin. The column was washed with 2.5 l of 50% (v/v) methanol and elution was carried out with 1.5 l of methanol. After the methanol-eluted fraction was concentrated under reduced pressure, water was added to make 300 ml. The mixture was extracted three times with 300 ml each of ethyl acetate. After being dehydrated over anhydrous sodium sulfate, the ethyl acetate layer was concentrated under reduced pressure, whereby about 10 g of a brown oily substance was obtained. The oily substance was developed with 6 l of chloroform using a column packed with 1 l of Wako Gel C-200 (a product of Wako Pure Chemical Industries, Ltd.) suspended in chloroform. KS-504a, KS-504b and KS-504e were eluted in the first eluted fractions (3 l) and KS-504d was eluted in the subsequently eluted franltions (3 l). The fractions containing KS-504a, KS-504b and KS-504e were concentrated under reduced pressure, and the concentrate was dissolved in a small quantity of a solvent mixture of hexane and chloroform (1:1 v/v). The solution was placed in a column packed with 500 ml of Wako Gel C-300 (a product of Wako Pure Chemical Industries, Ltd.) suspended in the solvent mixture having the composition described above, and eluted with 2.5 l of the same solvent mixture. The eluate was taken in 250 ml portions. KS-504a, KS-504b and KS-504e were eluted in fraction No. 7, fractions Nos. 8 and 9 and fraction No. 10, respectively.

The fraction No. 7 was concentrated under reduced pressure to give 451 mg of a colorless oily substance. The oily substance was dissolved in a small quantity of a solvent mixture of hexane and chloroform (1:1 v/v) and eluted with 500 ml of the same solvent mixture using a Lobar column (silica gel 60, size B, a product of Merck Inc.) which had been equilibrated with the same solvent mixture. The eluate was taken in 5 g portions, and the fractions containing KS-504a were combined and concentrated under reduced pressure. The concentrate was dissolved in a small quantity of hexane and crystallized in a cool and dark place. The crystals were filtered off and dryed to give 80 mg of KS-504a as colorless prism-like crystals.

The fractions Nos. 8 and 9 were combined and concentrated under reduced pressure to give 804 mg of a colorless oily substance. The oily substance was dissolved in a small quantity of a solvent mixture of hexane and chloroform (1:1 v/v) and eluted with 1.5 l of the same solvent mixture using a Lobar column (silica gel 60, size C, a product of Merck Inc.) which had been equilibrated with the same solvent mixture. The eluate was taken in 10 g portions, and the fractions containing KS-504b were combined and concentrated under reduced pressure. The concentrate was dissolved in a small quantity of chloroform, followed by addition of an appropriate amount of hexane. The mixture was allowed to stand in a cool and dark place for crystallization, and the resulting crystals were filtered off and dryed to give 92 mg of KS-504b as colorless needle crystals.

The fraction No. 10 was concentrated under reduced pressure to give 78 mg of a pale yellow oily substance. The oily substance was dissolved in a small quantity of a solvent mixture of hexane and chloroform (7:3 v/v) and eluted with 500 ml of the same solvent mixture using a Lobar column (silica gel 60, size B, a product of Merck Inc.) which had been equilibrated with the same solvent mixture. The eluate was taken in 5 g portions, and the fractions containing KS-504e were combined and concentrated under reduced pressure. The concentrate was dissolved in a small quantity of chloroform, followed by addition of an appropriate amount of hexane. The mixture was allowed to stand in a cool and dark place for crystallization, and the resulting crystals were filtered off and dryed to give 10 mg of KS-504e as colorless prism-like crystals.

The chloroform-eluted fractions containing KS-504d were concentrated under reduced pressure, and the concentrate was dissolved in a small quantity of methanol. The solution was placed in a column packed with 100 ml of YMC-ODS (a product of Yamamura Chemical Research Institute, 60-200 mesh) suspended in 70% methanol, and eluted with 300 ml of 70% methanol. All the eluted fractions were combined and concentrated under reduced pressure, and the concentrate was dissolved in a small quantity of chloroform. The solution was placed in a column packed with 400 ml of Wako Gel C-300 suspended in chloroform, and eluted with 2 l of chloroform. The eluate was taken in 10 g portions, and KS-504d was eluted in fractions Nos. 129 to 177. These fractions were combined and concentrated to dryness to give 510 mg of KS-504d as colorless powder.

During the foregoing purification steps, KS-504a, KS-504b, KS-504d and KS-504e were detected by thin layer chromatography using a silica gel plate containing a fluorescence agent (silica gel 60F$_{254}$, a product or Merck Inc.), followed by ultraviolet irradiation at 254 nm.

Example 2

KS-504a (104 mg) was dissolved in 2 ml of ethyl acetate containing 1.7N hydrogen chloride and subjected to reaction at 60° C. for 20 hours. After the reaction, water was added to the reaction solution and the ethyl acetate layer was separated. Then, the ethyl acetate layer was subjected to silica gel column chromatography by using a solvent mixture of chloroform and hexane (3:7 v/v) as the developing solvent. Crystallization was carried out by using hexane containing a small quantity of chloroform to give 48 mg of KS-504e.

Example 3 Tablets

A 10% hydroxypropylcellulose solution is added to a mixture consisting of 100 g of KS-504a, 40 g of lactose, 18 g of corn starch and 10 g of carboxymethylcellulose calcium, and the mixture is kneaded. The mixture is then granulated with an extrusion granulator with 1.0 mm screen, and the granules are dried at 60° C. The dried granules are screened on a 16-mesh sieve, and magnesium stearate is added to the granules to prepare tabletting granules According to the ordinary procedure, tablets, 8 mm in size, containing 100 mg of KS-504a in one tablet (170 mg) are prepared.

Example 4 Capsules

A 10% hydroxypropylcellulose solution is added to a mixture consisting of 50 g of KS-504a, 80 g of lactose and 38 g of potato starch, and the mixture is kneaded. The mixture is granulated in the same manner as in Example 3, and after addition of magnesium stearate, capsules containing 50 mg of KS-504a in one capsule (170 mg) are prepared according to the ordinary procedure.

Example 5 Soft Capsules

KS-504a (10 g) is dissolved in 100 g of soybean oil, and the solution is filled into capsules according to the ordinary procedure to prepare soft capsules each containing 10 mg of KS-504a.

Example 6 Tablets

A 10% hydroxypropylcellulose solution is added to a mixture consisting of 100 g of KS-504b, 40 g of lactose, 18 g of corn starch and 10 g of carboxymethylcellulose calcium, and the mixture is kneaded. The mixture is then granulated with an extrusion granulator with 1.0 mm screen, and the granules are dried at 60° C. The dried granules are screened on a 16-mesh sieve, and magnesium stearate is added to the granules to prepare tabletting granules. According to the ordinary procedure, tablets, 8 mm in size, containing 100 mg of KS-504b in one tablet (170 mg) are prepared.

Example 7 Capsules

A 10% hydroxypropylcellulose solution is added to a mixture consisting of 50 g of KS-504b, 80 g of lactose and 38 g of potato starch, and the mixture is kneaded. The mixture is granulated in the same manner as in Example 6, and after addition of magnesium stearate, capsules containing 50 mg of KS-504b in one capsule (170 mg) are prepared according to the ordinary procedure.

Example 8 Soft Capsules

KS-504b (10 g) is dissolved in 100 g of soybean oil, and the solution is filled into capsules according to the ordinary procedure to prepare soft capsules each containing 10 mg of KS-504b.

Example 9 Tablets

A 10% hydroxypropylcellulose solution is added to a mixture consisting of 200 g of KS-504d, 40 g of lactose, 18 g of corn starch and 10 g of carboxymethylcellulose calcium, and the mixture is kneaded. The mixture is then granulated with an extrusion granulator with 1.0 mm screen, and the granules are dried at 60° C. The dried granules are screened on a 16-mesh sieve, and magnesium stearate is added to the granules to prepare tabletting granules. According to the ordinary procedure, tablets, 9 mm in size, containing 200 mg of KS-504d in one tablet (270 mg) are prepared.

Example 10 Capsules

A 10% hydroxypropylcellulose colution is added to a mixture consisting of 100 g of KS-504d, 80 g of lactose and 38 g of potato starch, and the mixture is kneaded. The mixture is granulated in the same manner as in Example 9, and after addition of magnesium stearate, capsules containing 100 mg of KS-504d in one capsule (220 mg) are prepared according to the ordinary procedure.

Example 11 Soft Capsules

KS-504d (20 g) is dissolved in 100 g of soybean oil, and the solution is filled into capsules according to the ordinary procedure to prepare soft capsules each containing 20 mg of KS-504d.

Example 12 Tablets

A 10% hydroxypropylcellulose solution is added to a mixture consisting of 100 g of KS-504e, 40 g of lactose, 18 g of corn starch and 10 g of carboxymethylcellulose calcium, and the mixture is kneaded. The mixture is then granulated with an extrusion granulator with 1.0 mm screen, and the granules are dried at 60° C. The dried granules are screened on a 16-mesh sieve, and magnesium stearate is added to the granules to prepare tabletting granules. According to the ordinary procedure, tablets, 8 mm in size, containing 100 mg of KS-504e in one tablet (170 mg), are prepared.

Example 13 Capsules

A 10% hydroxypropylcellulose solution is added to a mixture consisting of 50 g of KS-504e, 80 g of lactose and 38 g of potato starch, and the mixture is kneaded. The mixture is granulated in the same manner as in Example 12, and after addition of magnesium stearate, capsules containing 50 mg of KS-504e in one capsule (170 mg) are prepared according to the ordinary procedure.

Example 14 Soft Capsules

KS-504e (10 g) is dissolved in 100 g of soybean oil, and the solution is filled into capsules according to the ordinary procedure to prepare soft capsules each containing 10 mg of KS-504e.

Example 15 Ointment

KS-504e (20 g) is mixed with a mixture of white vaseline and liquid paraffin to prepare an ointment containing 100 mg/g of KS-504e.

The vosodilative activity of KS-504a, KS-504b and KS-504d is explained below, referring to Experimental Example 1 on inhibition of contraction using extirpated blood vessel preparations.

Experimental Example 1

(1) Method

White bastard rabbits (male, 2-3 kg) were incised along the abdominal median line. The aorta was cut out with a length of about 2-2.5 cm from the venter, and spiral strips with a width of 3-4 mm were prepared therefrom. The strips were ligated with silk yarn at both ends, and the lower end was connected to a stationary rod, whereas the upper end was connected to a tension transducer (TB-612T, a product of Nippon Koden Co., Ltd.). The strips were suspended under an initial tension of 1.5 g. The strips were soaked in a Krebs-Henseleit solution at 32° C. whose composition in g/l was NaCl: 6.92, KCl: 0.35, $MgSO_4.7H_2O$: 0.29, $CaCl_2.2H_2O$: 0.37, $KH_2PO_4$: 0.16, $NaHCO_3$: 2.1 and glucose: 1.0 in a Magnus tube, and a gas (95% $O_2$ and 5% $CO_2$) was introduced therein. After being stabilized for 1 to 2 hours, the preparations were used for the experiment. Potassium chloride was added to the Magnus tube to a final concentration of 20 mM. The resulting contraction reaction was recorded on a polygraph (AM-6000, a product of Nippon Koden Co., Ltd.) in equal scales through the tension transducer. KS-504a, KS-504b and KS-504d were each dissolved in dimethyl sulfoxide to a concentration of 10 ,g/ml, and the solutions were properly diluted with a Krebs-Henseleit solution and added to the Magnus tube 30 minutes before the application of the contracting substance.

(2) Test results

TABLE 2

| Compound | Final concentration (μg/ml) | Rate of inhibition of contraction* (%) |
|---|---|---|
| KS-504a | 0.1 | 37 |
|  | 1.0 | 59 |
|  | 3.0 | 82 |
| KS-504b | 1.0 | 76 |

TABLE 2-continued

| Compound | Final concentration (μg/ml) | Rate of inhibition of contraction* (%) |
|---|---|---|
|  | 3.0 | 80 |
|  | 10.0 | 100 |
| KS-504d | 10.0 | 6.9 |
|  | 30.0 | 91 |

*The rate of inhibition of contraction was calculated according to the following equation.

$$\text{Rate of inhibition of contraction (\%)} = \left(1 - \frac{\text{Degree of contraction in the presence of a test compound}}{\text{Degree of contraction in the absence of a test compound}}\right) \times 100$$

As shown in Table 2, KS-504a, KS-504b and KS-504d inhibited the contraction of rabbit aorta, depending on the concentration.

The activity of KS-504e to inhibit histamine secretion is explained below, referring to Experimental Example 2.

Experimental Example 2

Influence on histamine secretion from rat peritoneal exudate cells (1) Preparation of suspension of rat abdominal cavity cells and histamine secretion Rats with body weights of 150-180 g were killed under dry ether anesthesia by exsanguination, and mast cell medium prepared according to the method of Sullivan, et al. [J. Immunol. 114, 1473 (1975)] (hereinafter abbreviated as MCM, composition: 150 mM NaCl, 3.7 mM KCl, 3 mM $Na_2HPO_4$, 3.5 mM $KH_2PO_4$, 1 mM $CaCl_2$, 5.6 mM glucose, 0.1% bovine serum albumin, 10 U/ml heparin) was injected intraperitoneally into the animals at 6 ml/animal. The abdominal parts were massaged for two minutes, and then cut open to sample exuded solution in the abdominal cavities. The exuded solution collected from 6 rats was centrifuged at 100×g for 5 minutes at 4° C., and the precipitate was mixed with an appropriate amount of water-cooled MCM, and washed three times to prepare a cell suspension (peritoneal exudate cells, hereinafter abbreviated as PEC) containing mast cells at a final concentration of about $3 \times 10^4$ cells/ml. Identification of mast cells was carried out by staining intracellular granules with 0.05% Toluidine Blue. Then, 1 ml of the thus obtained PEC was preincubated at 37° C. for 10 minutes, and then admixed with 0.1 ml of test solutions at various concentrations and incubated for 10 minutes. The incubated mixtures were further admixed with 0.1 ml each of 100 μg/ml phosphatidyl-L-serine and 1000 μg/ml concanavalin A, followed by incubation for 15 minutes. The reaction was discountined by addition of 3 ml of ice-cooled physiological saline solution, and the mixture was centrifuged at 1100×g for 10 minutes at 4° C. to obtain a supernatant and a residue. Histamine contents of the supernatant and the residue were measured by fluorometry according to the method of Komatsu [Allergy 27, 67 (1978)].

The histamine secretion rate was defined by a percentage of histamine content in the supernatant to total histamine content in the cells. The rate of suppression of histamine secretion by the test solution was calculated according to the following equation.

Rate of suppression of secretion (%) =

$$\left(1 - \frac{\text{Histamine secretion in the presence of a test compound} - \text{Spontaneous secretion}}{\text{Histamine secretion in the absence of a test compound} - \text{Spontaneous secretion}}\right) \times 100$$

TABLE 3

| Concentration of test solution ($\mu$g/ml) | Rate of suppression of histamine secretion (%) |
| --- | --- |
| 0.03 | 15 |
| 0.1 | 62 |

TABLE 3-continued

| Concentration of test solution ($\mu$g/ml) | Rate of suppression of histamine secretion (%) |
| --- | --- |
| 0.3 | 100 |

What is claimed is:

1. A compound represented by the formula (III):

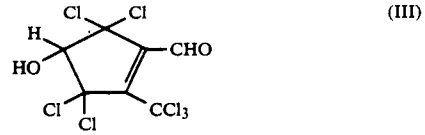

2. A pharmaceutical composition comprising as active ingredient an effective amount of compound as defined in claim 1 and at least one pharmaceutically acceptable carrier or excipient.

* * * * *